United States Patent
Randall et al.

(10) Patent No.: US 7,491,237 B2
(45) Date of Patent: Feb. 17, 2009

(54) ALLOGRAFT IMPLANT

(75) Inventors: Brandon L Randall, West Chester, PA (US); Roger D Goodwin, Clarks Summit, PA (US); Dominique Messerli, Downington, PA (US); Jacqueline Myer, Pottstown, PA (US); Robert J Delurio, Aston, PA (US); Michael L Boyer, II, Malvern, PA (US); Christopher M Angelucci, Schwenkesville, PA (US)

(73) Assignee: Synthes USA, LLC, West Chester, PA (US)

( * ) Notice: Subject to any disclaimer, the term of this patent is extended or adjusted under 35 U.S.C. 154(b) by 88 days.

(21) Appl. No.: 11/093,111

(22) Filed: Mar. 28, 2005
(Under 37 CFR 1.47)

(65) Prior Publication Data

US 2005/0240267 A1 Oct. 27, 2005

Related U.S. Application Data

(60) Provisional application No. 60/556,860, filed on Mar. 26, 2004.

(51) Int. Cl.
*A61F 2/44* (2006.01)
(52) U.S. Cl. .................................. 623/17.11
(58) Field of Classification Search ............... 623/17.11
See application file for complete search history.

(56) References Cited

U.S. PATENT DOCUMENTS

| | | |
|---|---|---|
| 6,025,538 A | 2/2000 | Yaccarino |
| 6,200,347 B1 | 3/2001 | Anderson et al. |
| 6,258,125 B1 | 7/2001 | Paul et al. |
| 6,270,528 B1 * | 8/2001 | McKay ............ 623/17.11 |
| 6,371,988 B1 | 4/2002 | Pafford et al. |
| 6,458,158 B1 | 10/2002 | Anderson et al. |
| 6,511,509 B1 | 1/2003 | Ford et al. |
| 7,048,765 B1 | 5/2006 | Grooms et al. |
| 2001/0032017 A1 * | 10/2001 | Alfaro et al. ............ 623/17.11 |
| 2002/0029084 A1 | 3/2002 | Paul et al. |
| 2002/0106393 A1 * | 8/2002 | Bianchi et al. ............ 424/423 |
| 2003/0083747 A1 | 5/2003 | Winterbottom et al. |
| 2003/0105528 A1 | 6/2003 | Shimp |
| 2003/0139815 A1 | 7/2003 | Grooms et al. |
| 2003/0144743 A1 | 7/2003 | Edwards et al. |
| 2006/0241763 A1 | 10/2006 | Paul et al. ............ 623/17.11 |
| 2007/0208424 A1 | 9/2007 | Messerli et al. ........... 623/17.11 |

* cited by examiner

*Primary Examiner*—Dave Willse
*Assistant Examiner*—Javier G Blanco
(74) *Attorney, Agent, or Firm*—Stroock & Stroock & Lavan LLP

(57) ABSTRACT

An allogenic implant for use in intervertebral fusion is formed from one or more two pieces. The pieces are made from bone, and are joined together to form an implant having sufficient strength and stability to maintain a desired distance between first and second vertebrae in a spinal fusion procedure. The implant pieces may be formed of cortical bone and connected by dovetail joints, and at least one cortical bone pin may be provided to lock the pieces together and to add strength to the implant. Teeth are formed on the vertebra engaging surfaces of the implant prevent short-term slippage of the implant.

28 Claims, 11 Drawing Sheets

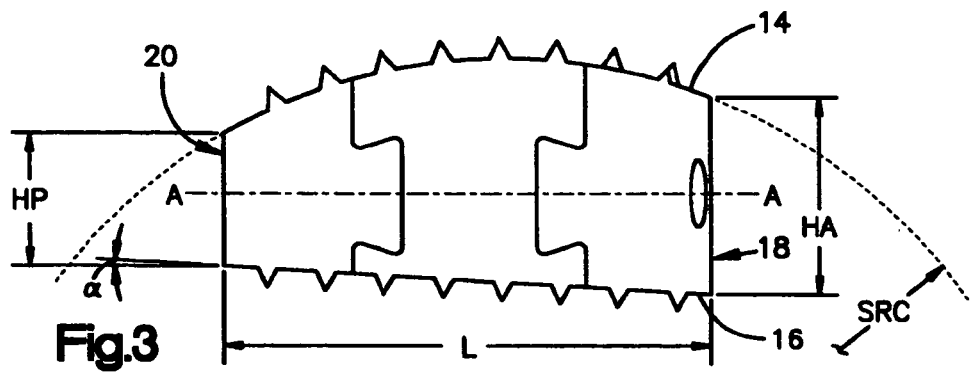
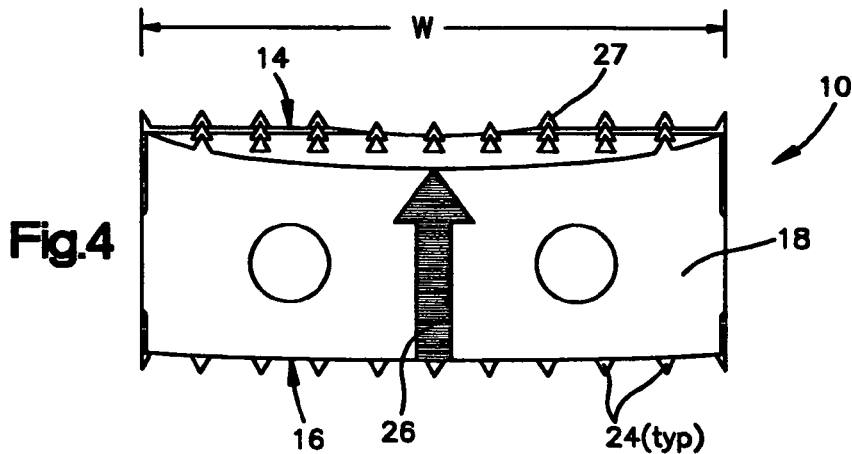
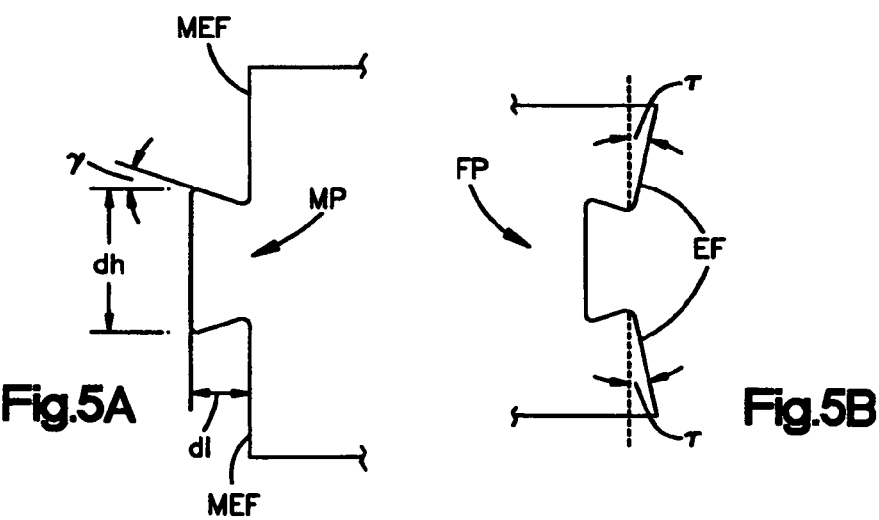

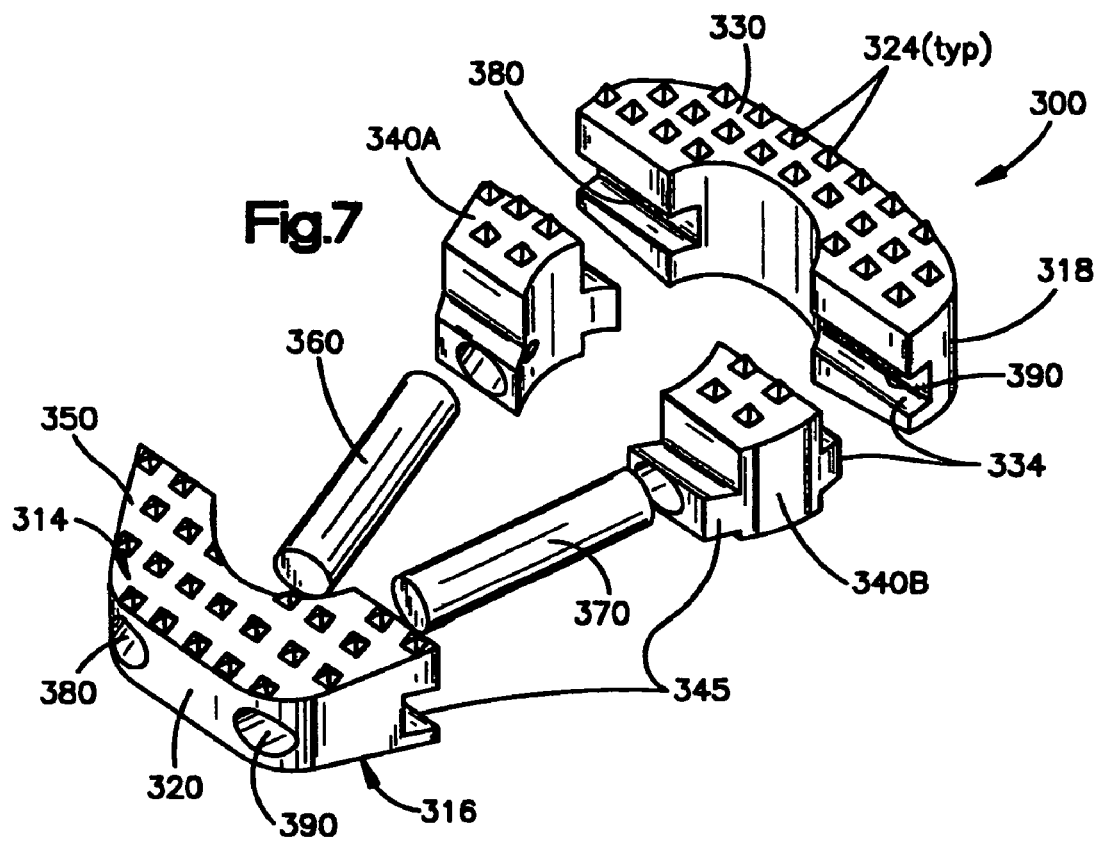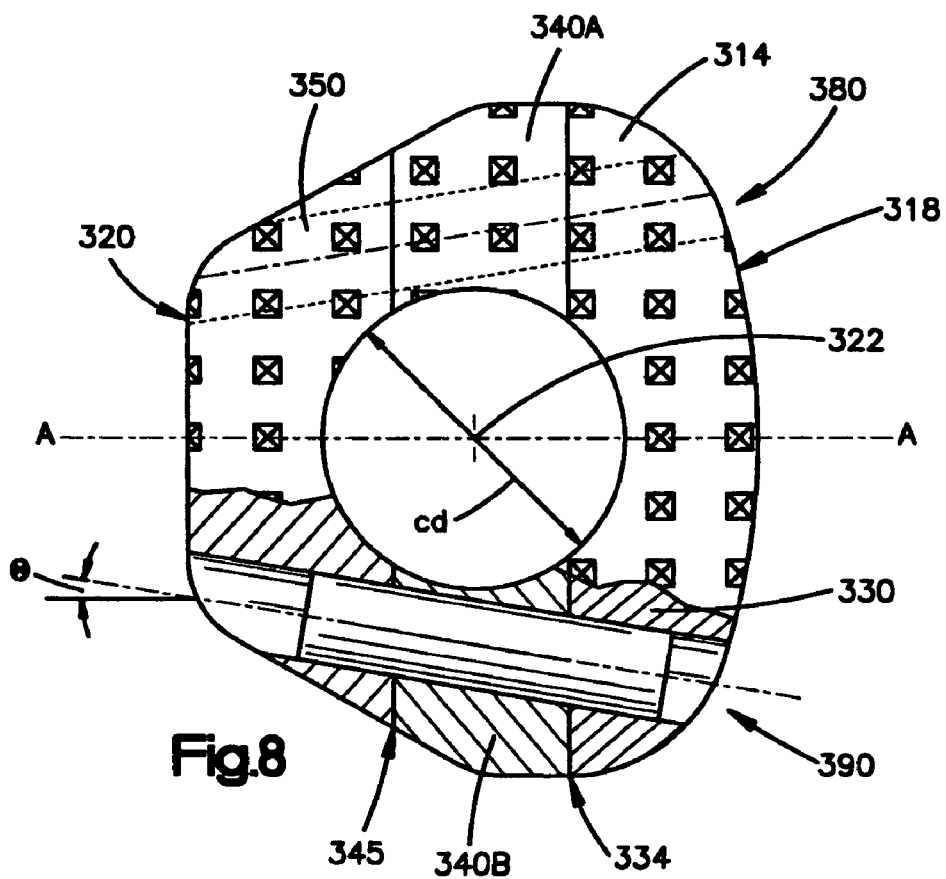

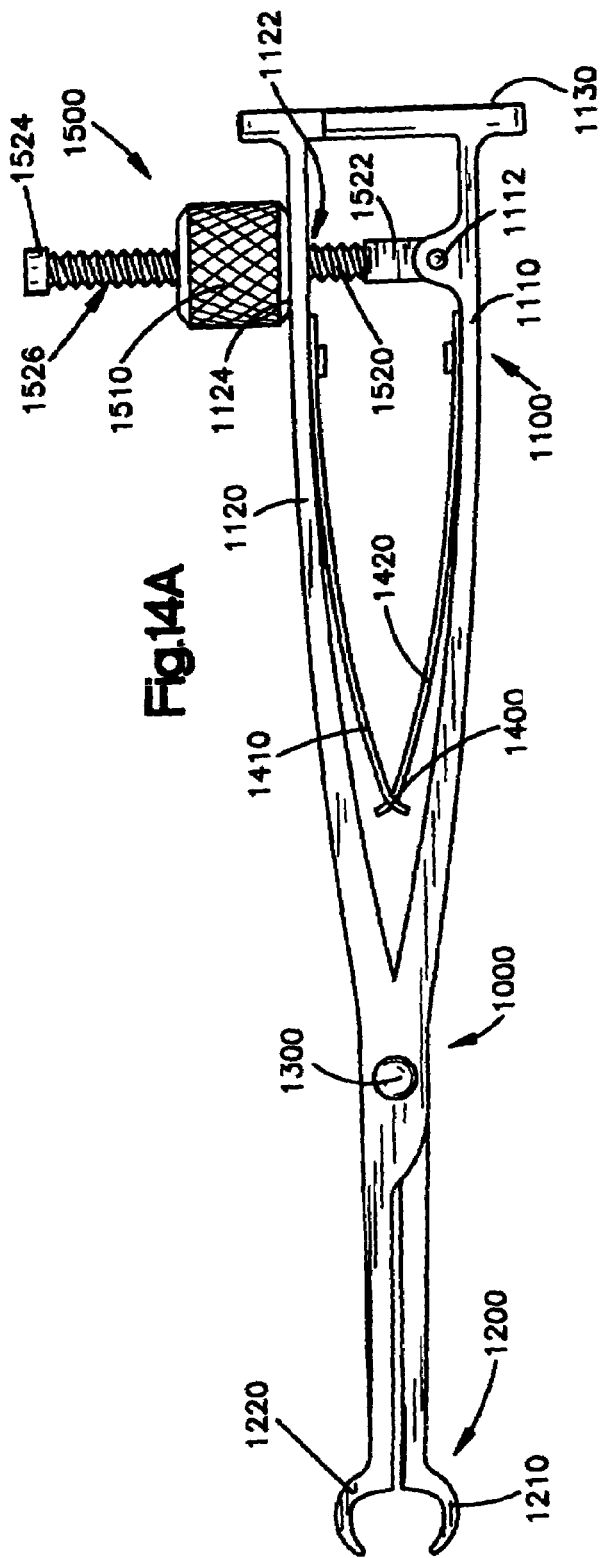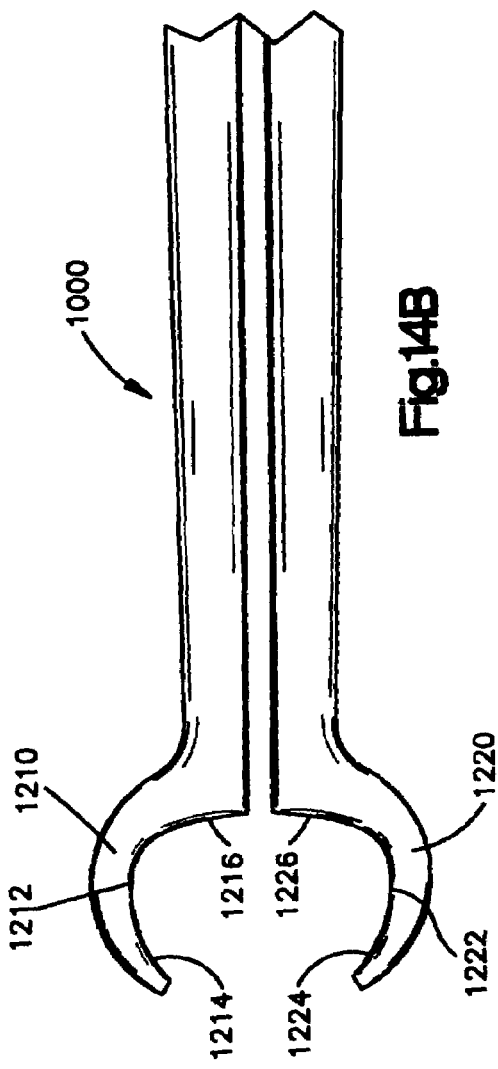

ALLOGRAFT IMPLANT

CROSS-REFERENCE TO RELATED APPLICATION

This application claims the benefit of U.S. Provisional Application No. 60/556,860, filed on March 26, 2004, entitled "MULTIPIECE CORTICAL ALLOGRAFT IMPLANT," the contents of which is incorporated in its entirety by reference herein.

FIELD OF THE INVENTION

The present invention is directed to an allogenic implant and, more particularly, to an allogenic intervertebral implant for the fusion of vertebrae.

BACKGROUND OF THE INVENTION

A number of medical conditions, such as compression of spinal cord nerve roots, degenerative disc disease, and trauma can cause severe back pain. Intervertebral fusion is a surgical method of alleviating back pain. In intervertebral fusion, two adjacent vertebral bodies are fused together by removing the affected intervertebral disc and inserting an implant that would allow for bone to grow between the two vertebral bodies to bridge the gap left by the removed disc.

A number of different implants and implant materials have been used for fusion with varying success. Current implants for intervertebral fusion include metallic cages, radiolucent implants and allografts. Metallic cages suffer from the disadvantage of requiring drilling and tapping of the vertebral endplates for insertion. In addition, the incidence of subsidence in long term use is not known. Due to MRI incompatibility of metallic cages, determining fusion is problematic. Radiolucent implants require the inclusion of metal or radiopaque markers to allow the surgeon to determine the adequacy of fusion, but like metallic cages radiolucent implants are not as readily integrated into the patient's bone structure as are allografts.

Allografts are sections of bone usually taken from long bones, such as the radius, ulna, fibula, humerus, tibia, or femur of a donor. A portion of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They also promote the formation of bone, i.e., are osteoconductive, and are also MRI compatible so that fusion of the adjacent vertebrae can be more accurately ascertained. Although the osteoconductive nature of the allograft provides a biological interlocking between the allograft and the vertebrae for long term mechanical strength, initial and short term mechanical strength of the interface between the allograft and the vertebrae needs to be addressed to minimize the possibility of the allograft being expelled after implantation.

Most allografts are simply sections of bone which, although cut to the approximate height of the disc being replaced, have not been sized and/or machined on the exterior surface to have a uniform shape. As a result, the fusion of the vertebral bodies does not occur in optimal anatomic position or in a consistent manner along the surface of the vertebral endplates. While a surgeon may perform some minimal intra-operative shaping and sizing to customize the allograft to the patient's spinal anatomy, significant and precise shaping and sizing of the allograft during the procedure is not possible due to the nature of the allograft. Even if extensive shaping and sizing were possible, a surgeon's ability to manually shape and size the allograft to the desired dimensions is limited.

With respect to the overall structure of a given bone, the mechanical properties vary throughout the bone. For example, a long bone (leg bone) such as the femur has both cortical bone and cancellous bone. Cortical bone, the compact and dense bone that surrounds the marrow cavity, is generally solid and thus carries the majority of the load in long bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10-20 MPa and a density of about 0.7, cortical bone has a tensile strength of about 100-200 MPa and a density of about 2. Additionally, the strain to failure of cancellous bone is about 5-7%, while cortical bone can only withstand 1-3% strain before failure. It should also be noted that these mechanical characteristics may degrade as a result of numerous factors such as any chemical treatment applied to the bone material, and the manner of storage after harvesting but prior to implantation (i.e. drying of bones).

The superior structural properties of cortical bone (as compared to cancellous bone) make it desirable for use as a spinal fusion implant. Thus, cortical bone implants may be obtained by taking a cross-section of the diaphysis of any one of the aforementioned long bones. The resulting cross-sectional implant will have a solid ring of cortical bone and a hollow center portion (the medullary canal of the long bone) that is suitable for packing with osteogenic materials, such as blood or allograft. Only a certain portion of each long bone, however, has the dimensions suitable for making cortical ring implants. The substantial remaining cortical portions of each long bone (e.g. the end portions such as the methaphysis) thus may remain unused for making structural cortical allograft implants.

Thus, there is a need to provide an allograft implant having similar dimensional and structural properties to traditional cortical ring allografts, but which is made up of multiple pieces of cortical bone that might otherwise remain unused for such structural allograft implants.

SUMMARY OF THE INVENTION

The present invention relates to an allogenic intervertebral implant for use when surgical fusion of vertebral bodies is indicated. The implant preferably comprises a wedge or plug conforming in size and shape with the end plates of adjacent vertebrae and has a plurality of teeth positioned on the top and bottom surfaces for interlocking with the adjacent vertebrae. The teeth preferably have a pyramid shape or a saw-tooth shape.

The implant preferably is comprised of a monolithic portion of cortical bone. In one embodiment, however, the implant may be comprised of two or more pieces of cortical bone. The two or more sections may be attached by a dovetail joint. One or more pins may also be used to prevent the sections from sliding out of connection with each other. The pins may be made of allogenic bone.

The implant preferably has teeth on the surfaces of the implant that will engage the vertebral end plates. The teeth are configured to bite into the bone of the vertebral end plates to resist expulsion of the implant subsequent to insertion.

The implant may take on various profiles and exterior geometries, depending upon the area of the spine that is to be treated. The implant may further be shaped with various thicknesses, to maintain the proper distance between the vertebrae being treated.

The present invention relates to an allogenic intervertebral implant for use when surgical fusion of vertebral bodies is indicated. The implant may generally comprise a wedge or plug of bone conforming in size and shape with the end plates of adjacent vertebrae and may have a plurality of teeth positioned on the top and bottom surfaces for interlocking with the adjacent vertebrae. The teeth may have a pyramidal or saw-tooth shape.

The implant may be made of a monolithic portion of cortical bone. Alternatively the implant may be comprised of two or more pieces of cortical bone. The two or more pieces of bone may be attached by a dovetail or other joint. One or more fasteners or pins may be used to prevent the sections from sliding out of connection with each other. The pins may be made of allogenic cortical bone.

The implant may have teeth on the surfaces of the implant that will engage the vertebral end plates. The teeth may be configured to bite into the bone of the vertebral end plates to resist expulsion of the implant subsequent to insertion.

The implant may take on various profiles and exterior geometries, depending upon the area of the spine that is to be treated. The implant may further be shaped with various thicknesses, to maintain the proper distance between the vertebrae being treated.

17 A multipiece implant may be provided having superior and inferior surfaces for engaging the end plates of adjacent vertebra of a patient's spinal column. The implant may comprise at least first and second cortical bone segments, where each segment has a locking surface configured to engage the locking surface of the other segment. Each segment further may have a pair of vertebra-engaging surfaces and at least one fastener-engaging surface. At least one fastener may be provided for engaging the bone segments. The locking surfaces of the first and second bone segments may comprise corresponding male and female surfaces, and the fastener may be configured to contact the fastener-engaging surfaces of the first and second bone segments to lock the segments together to form a multipiece implant having mechanical properties substantially similar to those of an implant formed of a single piece of cortical bone.

The locking surfaces of the first and second bone segments may comprise a dovetail joint. Alternatively, the locking surfaces may comprise a tongue and groove joint. Further, the vertebra-engaging surfaces of each cortical bone segment comprise a plurality of teeth, and these teeth may be arranged in a two dimensional array, where at least some of the teeth have a pyramidal shape.

The superior surface of the implant may have a substantially convex curvature, and both the superior and inferior surfaces may each comprise a plurality of teeth. The teeth may also be arranged in a two dimensional array, and the teeth may have a pyramidal shape.

The superior surface and the inferior surface may have a convex curvature in the medial-lateral plane.

The fastener may comprise a pin made of cortical bone, and the locking element engaging surface of each cortical bone segment may comprise at least one bore configured to receive the cortical bone pin. The implant may also have an anterior-posterior axis, and the at least one bore may be aligned substantially parallel to the axis. Alternatively, the at least one bore is aligned substantially non-parallel to the axis.

The implant may have superior and inferior engaging surfaces configured to engage adjacent vertebral end plates, and the implant further have an opening in communication with the superior and inferior engaging surfaces and configured to receive osteogenic material.

The implant may further comprise an anterior-posterior axis, a second cortical locking pin, and a second fastener engaging surface comprising a second bore configured to receive the second cortical locking pin. At least one of the first and second bores may be aligned substantially non-parallel to the anterior-posterior axis. The first and second bores may be arranged so that they do not intersect the opening and the bores may also be oriented to allow at least one dimension of the opening to be maximized.

The fastener may comprise a cortical bone pin and the fastener engaging surface of each bone segment may comprise a bore configured to receive the cortical bone pin, the fastener engaging surface of at least one bone segment further may comprise an abutting surface configured to engage an end surface of the cortical bone pin. The first and second bone segments of the implant may comprise an anterior bone segment and a center bone segment, respectively. The implant may further comprise a posterior bone segment engaged to the center bone segment via a dovetail joint, wherein the abutting surface is arranged on the posterior bone segment so that when the implant is placed between vertebral end plates of a patient, the pin is thereafter prevented from migrating in the posterior direction. Alternatively, the abutting surface may be located in the anterior bone segment so that when the implant is placed between vertebral end plates of a patient, the pin is thereafter prevented from migrating in the anterior direction.

A method of manufacturing an intervertebral implant is also provided. The implant may have superior and inferior surfaces, as well as an exterior surface. The method may comprise the steps of: forming at least first, second and third implant pieces from cortical bone; connecting the first and second pieces using a joint having a male element disposed on one of the first and second pieces and a corresponding female element disposed on the other of the first and second pieces; connecting the second and third pieces using a joint having a male element disposed on one of the second and third pieces and a corresponding female element disposed on the other of the second and third pieces; locking the first, second and third pieces together using a cortical bone pin disposed within bores formed through at least a portion of each piece to form an implant configured to be inserted between adjacent vertebra of a patient's spinal column; and forming superior and inferior vertebra engaging surfaces on the implant, wherein the engaging surfaces each comprise a plurality of teeth.

The step of forming a first piece may further comprise forming the male portion of a first dovetail joint, the step of forming a third piece may further comprise forming the male portion of a second dovetail joint, and the step of forming a second piece may further comprise forming opposing female portions of the first and second dovetail joints. The step of forming the first piece may further comprise marking an indicia on a face of the first piece, the indicia providing a visual indicia of implant orientation.

The indicia may comprise an arrow and the teeth may comprise pyramidal teeth. Furthermore, the superior vertebra engaging surface may have a convex profile. The superior and inferior vertebra engaging surfaces may also be oriented substantially non-parallel with respect to each other.

Subsequent to the step of locking the first, second and third pieces together, the implant may be machined so that the implant perimeter that substantially conforms to the outer perimeter of a patient's vertebral end plate. The implant may further have a medial-lateral centerline, and the cortical bone pin may be disposed within a bore that is oriented substantially non-parallel to the medial-lateral centerline.

The kit may also include an impacter for precisely positioning and impacting the implant between the vertebrae. The impacter may comprise a proximal hand gripping end and a distal implant-engaging end. The implant-engaging end may have an implant engaging face that is sized and dimensioned to engage the anterior face of the implant.

An intervertebral implant kit may be provided comprising: at least one implant configured for insertion between the end plates of adjacent vertebrae in the spinal column of a patient. The implant may comprise at least first and second cortical bone segments and may also have first and second vertebra engaging surfaces and a perimeter. At least one implant insertion tool may also be provided for engaging the implant and inserting the implant between the adjacent vertebrae, the tool having at least one implant engaging end configured to grip the implant. The perimeter of the implant may have an anterior segment configured to substantially conform to the anterior shape of the adjacent vertebral end plates when the implant is installed between the adjacent vertebrae, and the implant engaging end of the tool may further be configured to engage the implant along a substantial portion of the antenor segment.

The implant may further comprise a third cortical bone segment and at least a first fastener configured to lock the first, second and third bone segments together. The fastener may comprise a cortical bone pin. Further, at least one vertebra engaging surface of the implant may have a convex shape.

The implant may further comprise at least one opening in communication with at least one of the first and second vertebra engaging surfaces, and the opening may be configured to receive osteogenic, osteoinductive, or osteoconductive material. The implant may further comprise an anterior-posterior centerline, the fastener having an axis oriented at an acute angle with respect to the centerline. The intervertebral implant may also comprise a second fastener configured to lock the first, second and third bone segments together, the second fastener having an axis oriented at an acute angle with respect to the anterior-posterior centerline. Alternatively, the axes of the first and second fasteners may be oriented non-parallel with respect to each other.

The implant further comprising at least one through hole in communication with at least one of the first and second vertebra engaging surfaces and configured to receive bone growth enhancing materials, the implant further comprising a second fastener configured to lock the first, second and third bone segments together, wherein the first and second fasteners each have an axis, the axes oriented to maximize the size of the opening.

The vertebra engaging surfaces of the implant may comprise a plurality of protrusions configured to engage the respective vertebral end plate. The protrusions may comprise pyramidal shaped teeth.

The anterior segment of the implant may have first and second recesses, and the implant engaging end of the tool may have first and second protrusions for engaging the first and second recesses, wherein the recesses and protrusions are configured to allow the tool to firmly grip the implant.

The tool may further have first and second arms, the arms each having a proximal gripping end and distal implant-engaging end, wherein the first protrusion is disposed on the distal end of the first arm and the second protrusion is disposed on the distal end of the second arm. The tool may further comprise a pivot mechanism connecting the first and second arms at a location between the proximal and distal ends of the arms.

The first and second protrusions of the tool may engage the first and second recesses when the distal end of the tool contacts the anterior segment of the implant and the gripping ends of the first and second arms are moved toward each other.

The implant and the implant-engaging end of the tool may each comprise a medial-lateral dimension, and the medial lateral dimension of the tool may be equal to or less than the medial lateral dimension of the implant.

BRIEF DESCRIPTION OF THE DRAWINGS

FIG. 3 is a side view of the implant of FIG. 1;

FIG. 4 is an end view of the implant of FIG. 1;

FIGS. 5A and 5B are partial side views of the implant of FIG. 1;

FIG. 7 is an exploded view of a fourth exemplary embodiment of the implant according to the present invention;

FIG. 8 is a top view of the implant of FIG. 7;

FIGS. 14A and 14B are side and partial side views, respectively, of an implant insertion tool for use with the implant according to the present invention;

DETAILED DESCRIPTION OF THE INVENTION

Figure 1:
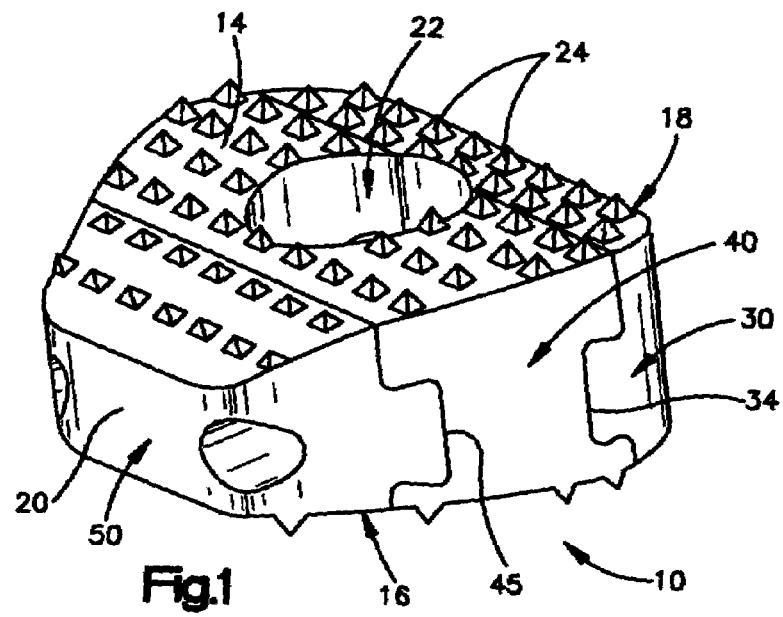
FIG. 1 is a perspective view of an exemplary embodiment of the implant according to the present invention.

FIGS. 1-4 show a first embodiment of an intervertebral cortical allograft implant 10 according to the present invention. Implant 10 preferably is shaped to conform in size and shape with at least a portion of the end plates of the vertebrae between which implant 10 is to be inserted. The outer periphery of implant 10 may be sized and shaped to match the outer periphery of the end plates of the vertebrae between which the implant 10 is to be used. Alternatively the outer periphery of the implant 10 may be sized and shaped to match only a portion of the outer periphery of the end plates of the vertebrae, or it may have an outer periphery that may not match the peripheral shape of the end plates of the vertebrae at any location.

Implant 10 generally comprises a superior surface 14, an inferior surface 16, an anterior face 18, a posterior face 20 and an opening 22. The implant 10 may be substantially symmetrical about a central axis "A-A" which connects and bisects the anterior and posterior faces 18, 20. The superior and inferior surfaces 14, 16 further may comprise teeth 24 disposed on at least a portion of each surface. Teeth 24 may be configured to engage the associated vertebral end plates to hold the implant securely in position when it is placed therebetween. In the illustrated embodiment, teeth 24 are discrete pyramidal projections having walls that form angles of approximately 60 degrees with respect to the plane of the respective superior or inferior surface 14, 16. It should be noted that although pyramidal shaped teeth 24 are illustrated, any appropriate tooth configuration may be provided, including discrete conically shaped teeth, continuous saw-tooth shaped patterns, or any other appropriate surface roughening or texturing known in the art.

Implant 10 may be formed by the connection of up to three discrete cortical bone segments 30, 40 and 50. In the illustrated embodiment, the anterior 30, center 40, and posterior 50 bone segments are connected via dovetail joints 34, 45 (FIG. 3). These dovetail joints 34, 45 are oriented substantially perpendicular to axis "A-A," in order to provide maximum resistance to a force applied along axis "A-A" tending to separate the segments. In the illustrated embodiment, female joint portion is provided on the center bone segment 40, with male joint portions provided on the anterior and posterior bone segments 30, 50. This orientation may be reversed, or may be provided in any appropriate combination on any of the bone segments. Likewise, although the dovetail joints are illustrated as being oriented substantially perpendicular to axis "A-A," these joints may be oriented at other appropriate angles with respect to the central axis.

Figure 19:
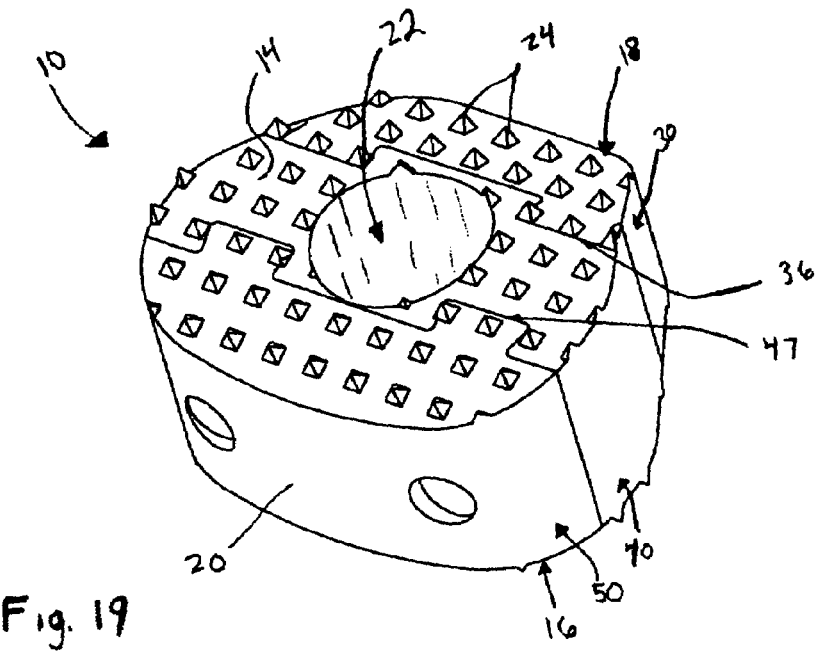
FIG. 19 is a perspective view of another exemplary embodiment of the implant according the present invention.

The dovetail joints may also be oriented on other surfaces of the bone segments. For example, the female and male joint portions may be provided on the superior and anterior surfaces of the implant. FIG. 19 shows dovetail joints 36, 47 on the superior surface 14 of the implant 10. In this embodiment, the dovetail joints 36, 47 are oriented in the same plane as opening 22. In the illustrated embodiment, female joint portion is provided on the center bone segment 40, and male joint portions are provided on the anterior and posterior bone segments 30, 50.

The implant 10 may further be provided with mechanical connectors 60, 70, which in the illustrated embodiment are cylindrical pins composed of cortical bone. These pins 60, 70 may be disposed in correspondingly-shaped bores 80, 90 formed through the cortical bone segments 30, 40 and 50. These pins may be oriented substantially parallel to the axis "A-A," and substantially perpendicular to the dovetail joints 34, 45 to provide maximum resistance to a force applied perpendicular to axis "A-A" tending to separate the segments. Cortical pins 60, 70 may also provide the implant with increased strength in bending as compared to a multipiece implant without pins.

Figure 9:
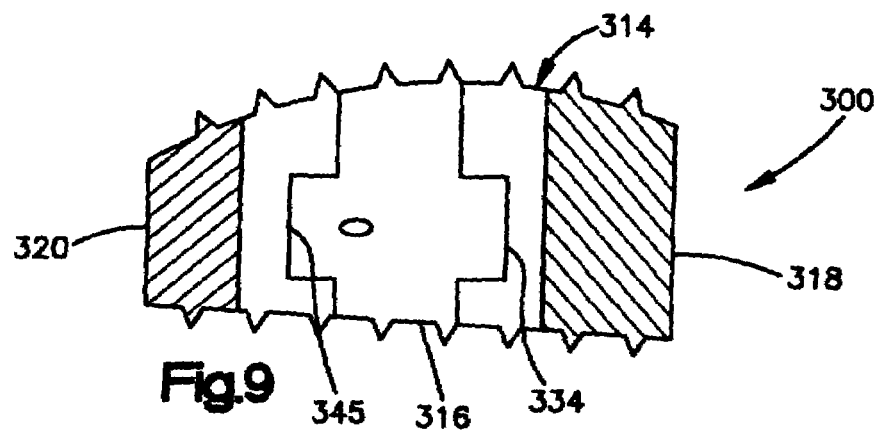
FIG. 9 is a side view of the implant of FIG. 7.
Figure 10:
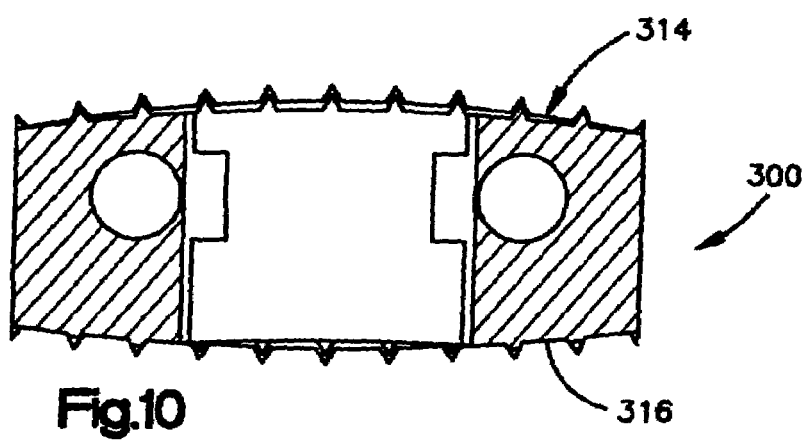
FIG. 10 is an end view of the implant of FIG. 7.
Figure 11:
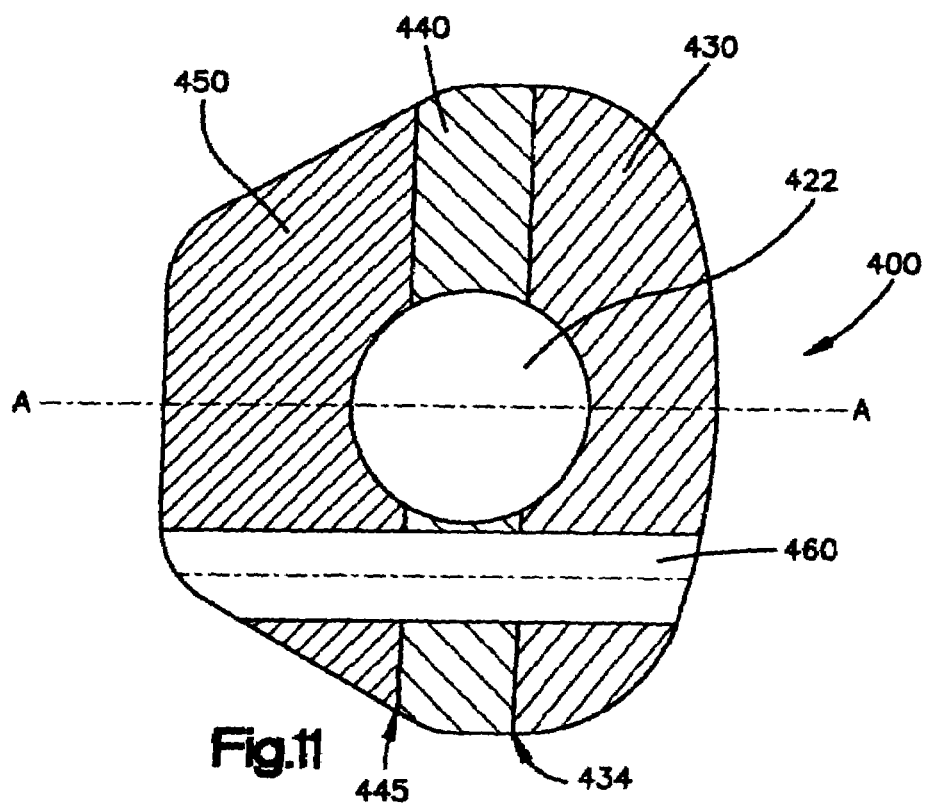
FIG. 11 is a top view of a fifth exemplary embodiment of the implant according to the present invention.

It is noted that although the implant 10 is shown as having two pins, an implant having a single pin may alternatively be provided (see FIG. 11). Such an implant may have a simplified construction, while still providing the implant with a desired strength in bending. In a further alternative embodiment, the cortical pin or pins 60, 70 may be oriented substantially non-parallel to the implant central axis "A-A," such that the pins may be oriented at angles up to and including about 15 degrees with respect to axis "A-A" (see FIGS. 7-9). In yet a further embodiment, an implant 10 may be provided with a pin or pins 60, 70 oriented substantially perpendicular to both axis "A-A" and to the superior and inferior surfaces 14, 16 of the implant 10 (see FIGS. 12-13).

Figure 20:
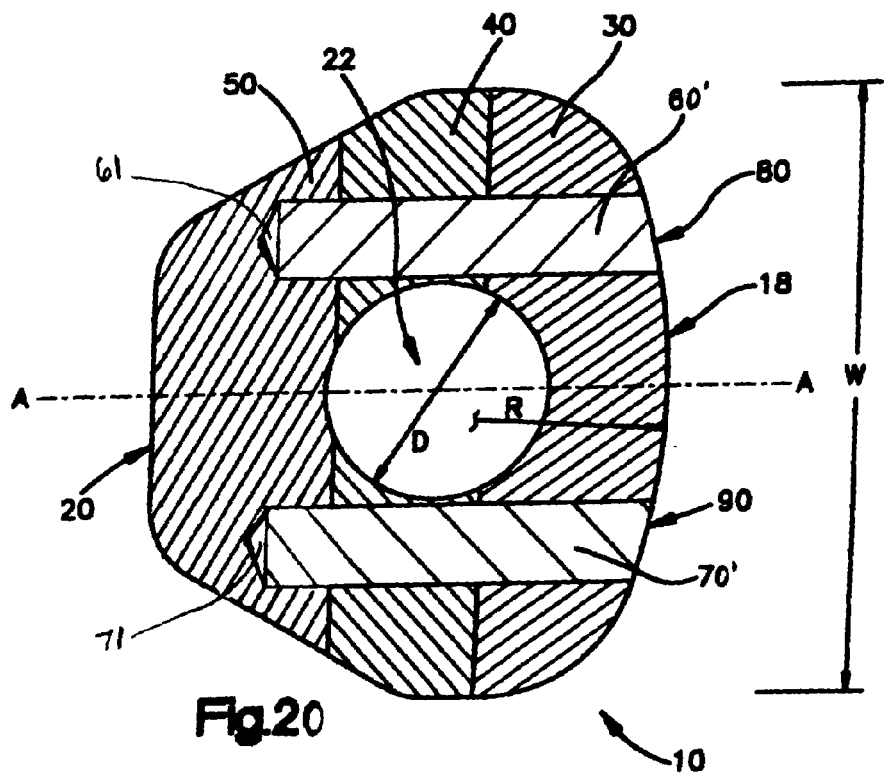
FIG. 20 is a top view of a further exemplary embodiment of the implant according to the present invention.

Moreover, with any of these embodiments, the pins 60, 70 and their respective bores 80, 90 may be formed so that the pins and holes go through the entire length (or height) of the implant, or they may be formed so that the pins and holes go through only a portion thereof. In one embodiment, the bores 80, 90 may go through the entire length of the anterior and central bone segments 30, 40, but may only go through a portion of the posterior bone segment 50 as shown in FIG. 20. Thus, the pins 60', 70' may abut an internal end surface of the posterior bone segment 50. In this illustrated embodiment, the cortical pins 60' and 70' may be machined to be cone shaped at the ends 61, 71 of the pins 60', 70' that abut the internal end surface of the posterior bone segment 50. Such an arrangement may have the advantage of guaranteeing that the cortical pins 60', 70' can not work themselves loose from the bone segments after insertion in the patient and move in the posterior direction toward the spinal canal. Such an internal abutting configuration could likewise be implemented for the anterior bone portion to prevent a loosened pin from moving anteriorly toward the patient's esophagus.

Figures 16A, 16B, 16C, 16D, 16E:
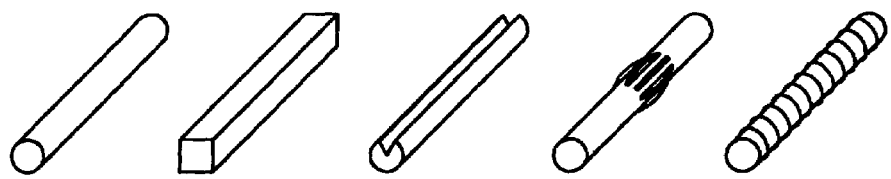
FIGS. 16A through 16E are perspective views of several designs for mechanical fasteners for use with the implants of FIGS. 1-15.

The cortical pins 60, 70 may take on any appropriate configuration, and may be secured within the implant in a variety of ways. For example, the fasteners 60, 70 may be secured within corresponding bores 80, 90 by a press fit. Alternatively, the pin or pins may have threads along at least a portion of their length which may mate with a correspondingly threaded bore or bores in the implant. The pin or pins may have any appropriate external geometric cross-sectional shape, such as circular (FIG. 16A), X-shaped, ovular, square (FIG. 16B), rectangular, etc., and may be accepted in bores having similar or different cross-sectional shapes. Likewise, the pins may assume a "split pin" arrangement (FIG. 16C), or the pin may have a series of alternating longitudinal grooves and raised radial portions (FIG. 16D). The pins may also have one or more circumferentially-disposed rib elements (FIG. 16E). Other pin designs may also be used as appropriate. The pin or pins may also be secured using an appropriate biocompatible adhesive. Any combination of such securing configurations may also be used. Such arrangements may keep the pins from separating from the implant either before, during or after implantation within a patient.

As will be apparent to one of ordinary skill in the art, each pin arrangement may provide individual advantages both in terms of manufacturability and implant integrity. These advantages will be described in more detail later in relation to the description of each individual embodiment.

Thus, when fully assembled, the pins 60, 70 and joints 34, 45 may provide a multipiece cortical bone implant 10 that may function substantially the same as an implant made of a single, monolithic piece of cortical bone.

Figure 2:
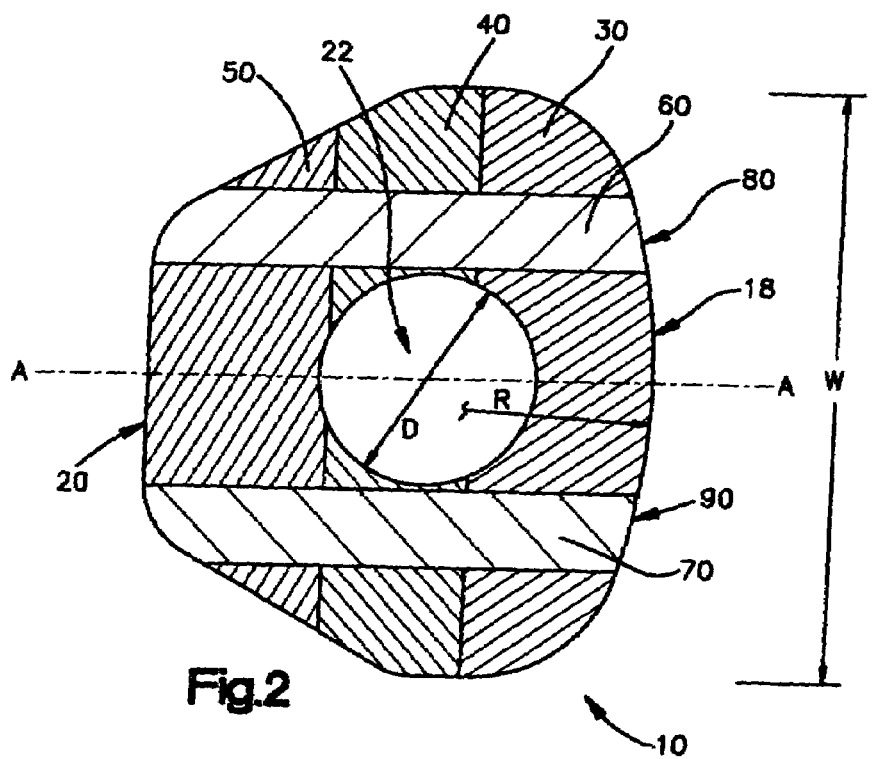
FIG. 2 is a top view of the implant of FIG. 1.
Figure 17:
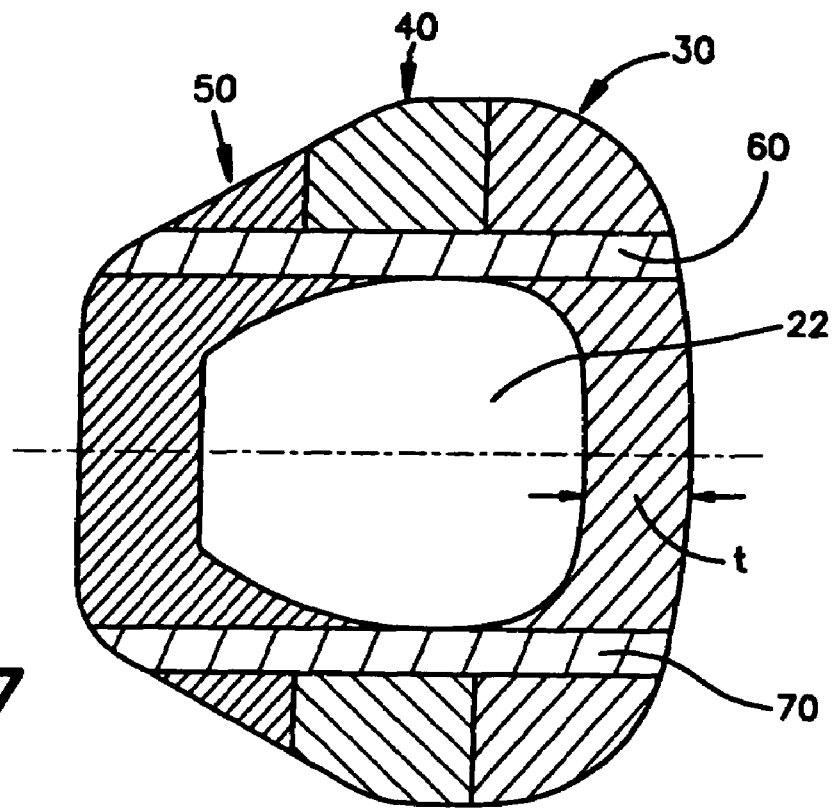
FIG. 17 is a top view of an eighth exemplary embodiment of the implant of the present invention.

As shown in FIGS. 2 and 3, the bone segments 30, 40 and 50 may be sized and dimensioned to result in an overall implant length "L" in the range of from about 10 millimeters (mm) to about 15 mm. In one embodiment, length "L" is about 12.5 mm. Likewise, the bone segments may be sized and dimensioned to result in an overall implant width "W" at its widest point that is within the range of from about 12 mm to about 18 mm. In one embodiment, width "W" may be about 15 mm. Opening 22 may have a diameter "D" of about 5.5 mm. An implant having such dimensions may be configured to fit within the endplates of the vertebra of the cervical spine. However, it will be understood that the implant 10 may have different dimensions than the ones described herein without departing from the spirit and scope of the invention. Furthermore, opening 22 may assume any of a variety of geometric shapes, including circular (as in FIGS. 1-3), square, rectangular, ovular, etc., or the opening 22 may have a non-geometric shape. Alternatively, opening 22 may consist of a plurality of discrete openings. In the embodiment shown in FIG. 17, the opening 22 is shaped to substantially match the external shape of the implant, thus providing an implant having a relatively constant wall thickness "t." The wall thickness "t" may be chosen from a value within the range of from about 2 mm to about 5 mm; and in one embodiment the thickness "t" may be about 3 mm. This arrangement may provide an implant having as large an opening as possible, to maximize the amount of osteogenic material that may be packed therein.

Figure 18:
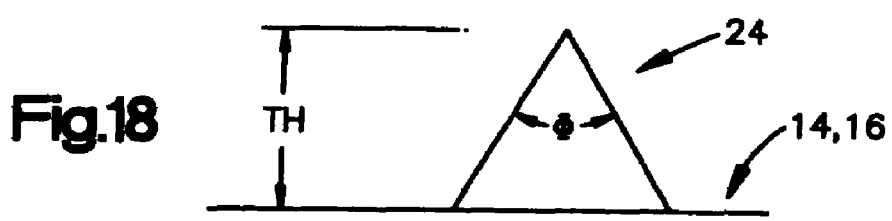
FIG. 18 is a side detail view of a pyramidal tooth for use in any one of the previous embodiments.

Implant 10 may comprise a plurality of teeth 24 formed over at least a portion of its superior and inferior surfaces 14, 16 that may provide a mechanical interlock between implant 10 and the end plates of the vertebrae to be treated. As shown in FIGS. 1, 3 and 4 teeth 24 may be formed in rows disposed over the entire superior and inferior surfaces 14, 16 and the teeth 24 may be pyramid shaped. As illustrated in FIG. 18, the pyramidal teeth may have a tooth angle "φ" formed from the tip to the base of approximately 60 degrees. The teeth may also have a tooth height "TH" chosen from a value in the range of from about 0.3 mm to about 0.7 mm. In one embodiment the tooth height "TH" is about 0.5 mm. As previously noted, however, these teeth 24 may take any appropriate configuration known in the art, both in profile and the pattern in which they are disposed over the superior and inferior implant surfaces of the implant. Because these teeth 24 are formed from cortical bone, they have sufficient strength and hardness to impale themselves into the vertebrae surfaces and provide an enhanced interlock with the adjacent vertebrae, thus preventing short-term slippage of implant 10 until implant 10 is fused with the vertebrae by the growth of new bone.

In the embodiment shown in FIGS. 1 to 4, superior surface 14 is convex and inferior surface 16 is flat. The convex superior surface 14 may have a radius of curvature in the range of from about 8 mm to about 25 mm. In one embodiment (FIG. 3), convex superior surface 14 may have a radius of curvature "SRC" of about 14 mm. The inferior surface 16 of this embodiment may form an angle α with respect to the central axis "A-A." Angle α may be within the range of from about 2 degrees to about 5 degrees. In one embodiment, α is about 3.5 degrees. Thus, the implant may have a greater height "HA" adjacent the anterior face 18 compared to the height "HP" adjacent the posterior face 20. Height "HA" may be within the range of from about 4 mm to about 11 mm, while height "HP" may be within the range of from about 2.4 mm to about 9.4 mm. Such a configuration provides a good fit with the natural contours of the normal cranial and caudal surfaces of the cervical vertebrae, while also restoring the desired natural lordosis between adjacent vertebrae.

In an alternative embodiment, both the superior and inferior surfaces may have a convex curvature in order to more closely conform the implant to the anatomy of the patient's vertebral end plates. Thus, in one embodiment the curvature of the superior surface may be disposed in the anterior-posterior plane, while the curvature of the inferior surface 16 may be disposed in the medial lateral plane. It will be appreciated, however, that other surface configurations may be provided to allow close conformity of the implant to the end plates.

Figure 6A:
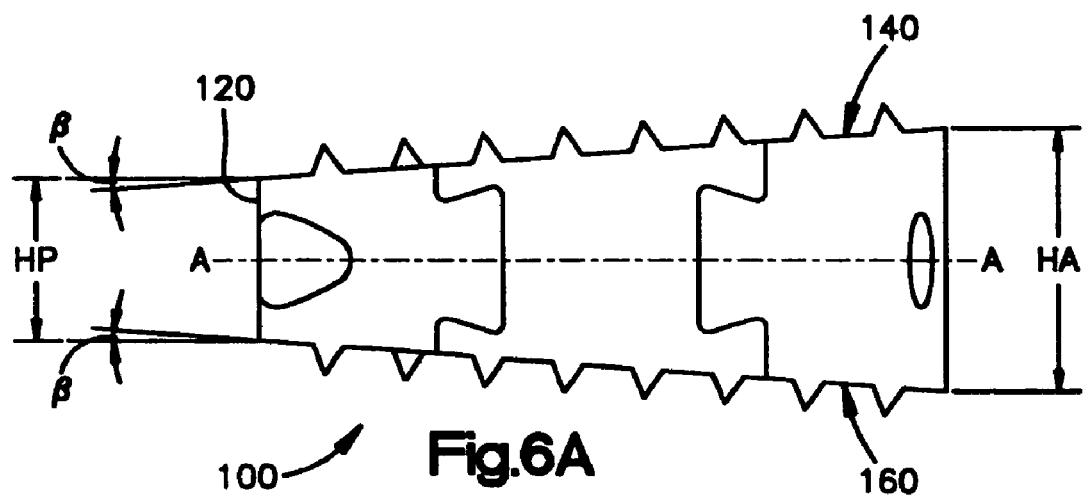
FIGS. 6A and 6B are side views of second and third exemplary embodiments of the implant according to the present invention.
Figure 6B:
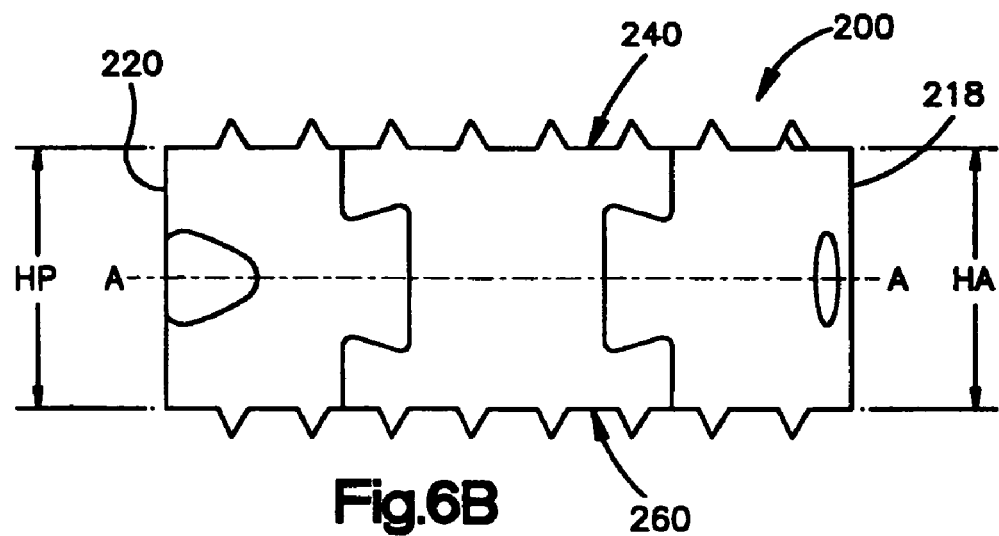

In an alternative embodiment shown in FIG. 6A, both the superior and inferior surfaces 140, 160, are flat, and each surface forms an angle β with respect to the central axis "A-A," thus providing an implant 100 having a wedge shape, with a height "HA" adjacent the anterior face 126 that is greater than the height "HP" adjacent the posterior face 128. Height "HA" may be within the range of from about 4 mm to about 11 mm, while height "HP" may be within the range of from about 2.5 mm to about 9.5 mm. Angle β may be within the range of from about 2 degrees to about 5 degrees. In one embodiment, β is about 3.5 degrees. In yet another embodiment, shown in FIG. 6B, both the superior and inferior surfaces 240, 260, are flat, and each is substantially parallel to the central axis "A-A," thus providing a substantially flat implant 200 in which the height "HA" and "HP" adjacent the anterior and posterior faces 218, 216, respectively. Heights "HA" and "HP" may be within the range of from about 4 mm to about 11 mm.

Figure 21:
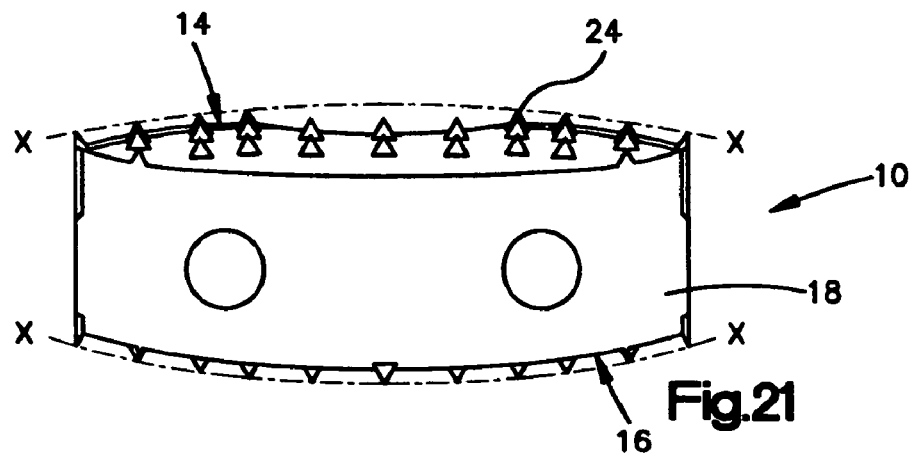
FIG. 21 is an end view of yet another exemplary embodiment of the implant according to the present invention.

The superior surface 14 and the inferior surface 16 may have the same or different curvatures in the same or different planes. For example, one surface may be convex and the other surface may be flat. Alternatively, in the embodiment shown in FIG. 21, the superior surface 14 and the inferior surface 16 have a convex curvature in the medial lateral plane as shown by lines X-X.

In all of the illustrated embodiments, typified in FIGS. 2 and 3, the implant 10 is formed so that anterior face 18 is curved, while posterior face 20 is flat. Anterior face 18 may have a radius of curvature "R" within the range of about 15 mm to about 25 mm. In one embodiment this radius is about 20 mm.

As illustrated in more detail in FIG. 5A, the male dovetail portion "MP" may have an anterior-posterior length "dl" of about 1.2 mm, a maximum superior-inferior height "dh" of about 5 mm, and a tail angle γ of about 25 degrees with respect to the implant central axis. The female dovetail portion may have similar dimensions. These dimensions may be adjusted as appropriate, and the clearances between the male and female portions may be selected to provide an interference fit it desired. The described dimensions will provide an interlocking of adjacent bone segments 30, 40, 50 to withstand expected forces of the spinal column to which the implant will be subjected after implantation.

An alternative embodiment of a dovetail joint for use in joining adjacent bone portions is illustrated in FIG. 5B, in which female portion "FP" has upper and lower engaging faces "EF" that are angled with respect to the vertical. Specifically, the engaging faces "EF" form an angle "τ," of about 2 degrees with respect to the respective male engaging faces "MEF" shown in FIG. 5A. Thus, when the male and female dovetail portions "MP," "FP" are fit together, the female portion may deflect slightly near the engaging faces "EF", thus providing a tight fit between the opposing bone portions. This feature may also provide the advantage of eliminating the gap that may form between the opposing bone pieces once the implant 10 has been freeze-dried, since the bone portions may shrink slightly during that process. The interference fit thus provided may lock the male and female portions "MP," "FP" together with sufficient force that cortical locking pins may not be needed to lock the implant together. A sufficiently tight interference fit may thus provide a simplified implant.

As previously noted, opening 22 may be shaped and configured to be as large as possible to maximize the amount of osteogenic, osteoconductive, or osteoinductive material that may be packed therein. Such material may speed fusion of the implant 10 with the opposing vertebra. A non-limiting list of such materials includes blood, bone chips, demineralized bone matrix, calcium phosphate bone cements, or any other osteogenic, osteoconductive or osteoinductive material known in the art.

As shown in FIG. 4, the anterior surface 18 of the implant 10 may have a vertical line 26 as an indicia of both the medial-lateral centerline of the implant and the anterior end of the implant. Since the implant may be rather small, such an indicia may aid the surgeon in fitting the implant to the installation tool. Alternatively, the implant 10 may be provided with a multidimensional indicia 27 which may additionally identify the superior and inferior surfaces of the implant. In the illustrated embodiment, an arrow is provided as identifying the medial-lateral centerline of the anterior face 18 of the implant 10 and which also identifies the proper superior-inferior orientation of the implant. Alternatively, other distinguishing indicia of implant orientation may be provided, such as an alphanumeric identifier or a word (e.g. "anterior"). Such markings 26, 27 may be applied using any appropriate biocompatible ink, or they may be etched into the surface of the implant.

With the above described geometries, implant 10 may ideally be used between cervical vertebrae. However, it can be readily seen by those skilled in the art that implant 10 may take on many different geometries to optimize its use between vertebrae in different areas of the spine.

FIGS. 7-10 illustrate an alternative embodiment of a multipiece cortical implant 300 comprising anterior, center, and posterior cortical bone segments 330, 340A, B and 350. As shown in FIG. 7, implant 300 has the same general shape as the previously described embodiments, including the rounded anterior face 318, flat posterior face 320, and opening 322. Moreover, superior and inferior surfaces 314, 316 have a plurality of vertebra-engaging teeth 324 disposed thereon.

The embodiment of FIGS. 7-10, however, has cortical pins 360, 370 that are oriented at an acute angle θ with respect to the implant central axis "A-A." Angle θ may be within the range of from about 12 degrees to about 18 degrees, and in one embodiment, θ is about 15 degrees. Thus, the distance between the bores 380, 390 may be greater at the anterior face 318 than at the posterior face 320. This arrangement allows for a larger opening 322 to be provided as compared to the previous embodiments, because the bores 380, 390 and pins 360, 370 of this embodiment are located farther apart where they pass through the center bone segment 340. Providing a larger opening 322 allows the surgeon to pack the implant with more osteoinductive or osteoconductive material than with the previous embodiments, thus increasing the likelihood that the implant will be successfully integrated into the adjacent vertebral elements. In one embodiment, opening 322 has a diameter "cd" of about 7.1 mm. It is noted that the center bone segment 340A, B is composed of two pieces due to the size of the opening. Such a two-piece center bone segment 340A, B does not detract from the structural integrity of the implant because each segment is captured by one cortical pin 360, 370.

The angled pins 360, 370 of this embodiment may also provide an additional locking feature not present with the parallel pins of the previous embodiments. Specifically, the angled pins may resist a force applied to the implant along axis "A-A" that would tend to separate the bone segments 330, 340, 350. With the previous embodiments, this was a function provided by the dovetail joints between the bone segments. Since the pins perform the anterior-posterior retention function in the present embodiment, the dove-tail joints 34, 35 between bone segments may be replaced with simpler tongue and groove joints 334, 345. Such tongue and groove joints are easier to manufacture and to fit together during implant assembly.

The implant 300 of this embodiment may be provided in any of the previously described superior and inferior surface profiles, such as convex, lordotic (parallel wedge) and parallel. The convex profile is specifically designed to fit the anatomy of the end plates of the vertebra. The lordotic profile is specifically designed to maintain the anatomical alignment of the spinal column. It will be appreciated that all other geometric configurations of the previous embodiments, including applicable pin and bore configurations, may be applied to the implant 300 of the present embodiment.

FIG. 11 illustrates an alternative embodiment of the invention in which implant 400 is provided with a single cortical pin 460 oriented substantially parallel to the implant central axis "A-A." The pin of this embodiment is located on one side of the opening 422, and, in combination with a pair of dovetail joints 434, 445 serves to lock the anterior, center, and posterior bone segments 430, 440, 450 together in a manner identical to that of the embodiment of FIG. 1. The implant 400 of this embodiment provides an advantage over previous embodiments in that it is simpler to manufacture and requires fewer total pieces. Furthermore, although the absence of a second cortical pin may render this implant slightly less strong in bending as compared to the dual pin embodiments of FIGS. 1-10, the bending strength of this implant 400 may still be sufficient to withstand the loads experienced in the spinal column in normal use. As with the embodiment of FIGS. 7-10, implant 400 may be provided with convex, lordotic and parallel engaging surface configurations. Likewise, all other geometric configurations of the previous embodiments, including applicable pin and bore configurations and pyramidal teeth configurations, may be implemented in implant 400.

Figure 12:
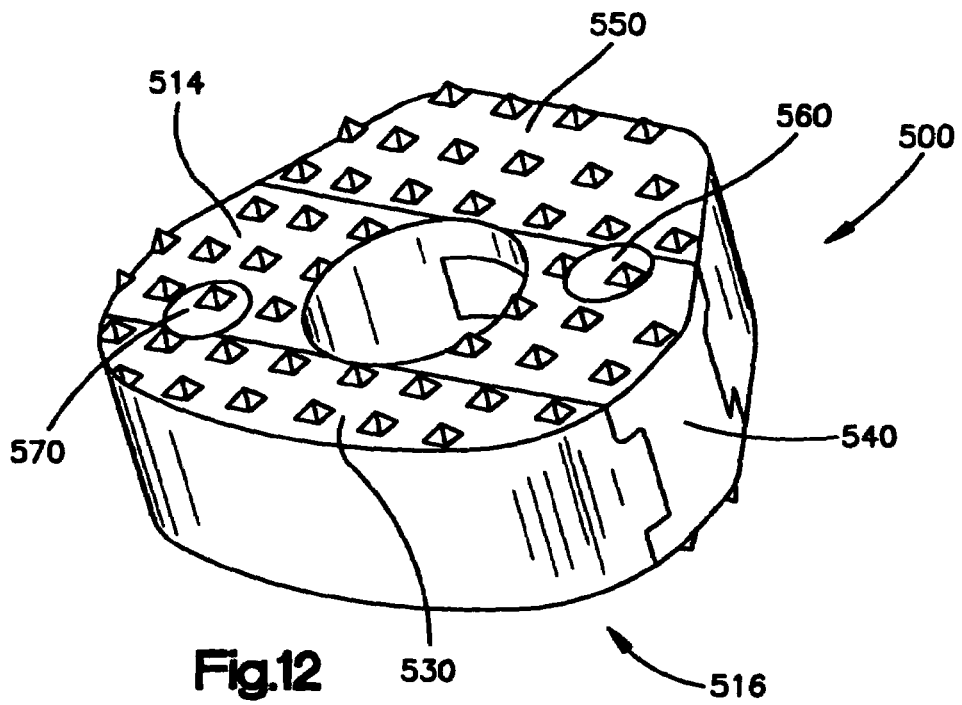
FIG. 12 is a top view of a sixth exemplary embodiment of the implant according to the present invention
Figure 13:
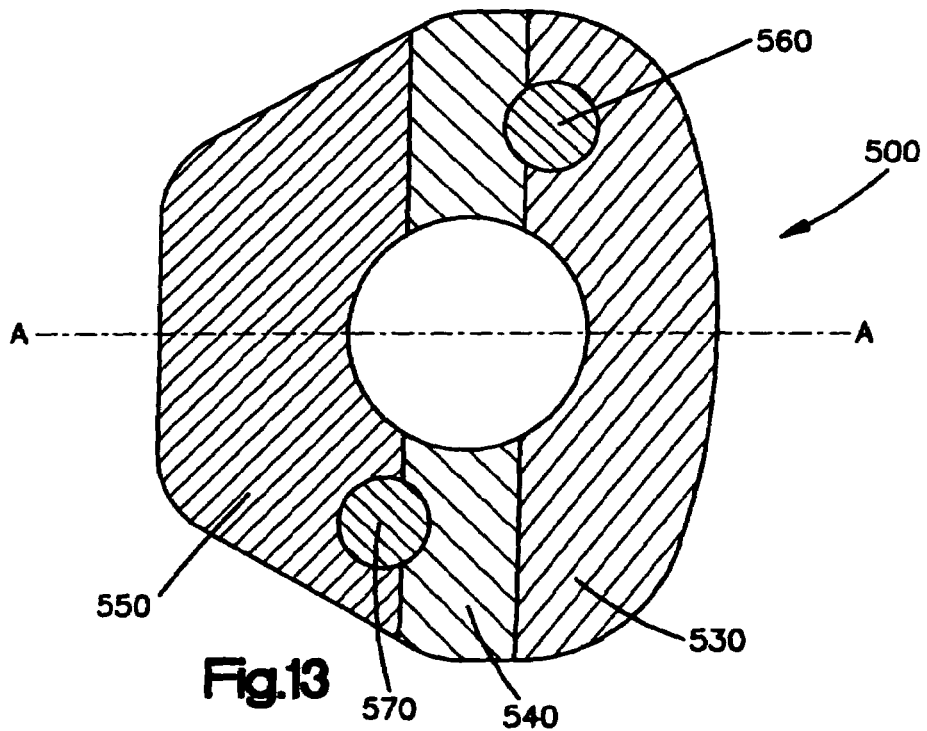
FIG. 13 is a top view of the implant of FIG. 12.

FIGS. 12 and 13 illustrates yet another embodiment of an implant 500 having a pair of vertically oriented pins 560, 570 for locking together adjacent bone segments 530, 540, 550. In this embodiment, pins 560, 570 are oriented substantially perpendicular both to the implant central axis "A-A" and to the superior and inferior surfaces 514, 516. This embodiment has the advantage that it may be easier to machine as compared to the horizontal pin embodiments because the bores may be located farther from the implant sides than in the horizontal pin embodiments, and thus the implant may be less likely to exhibit cracking during the machining operation. This embodiment also has the advantage that the cortical pins 560, 570 may function to bear at least a portion of the vertebral end-forces applied to the implant due to their general alignment with the superior-inferior axis upon insertion Furthermore, since the pins are vertically oriented, there is less chance that they might become loosened in the patient and migrate beyond the implant.

FIGS. 14A and 14B are side and partial side views, respectively, of an implant insertion tool 1000 for use with any of the previously described implants. As illustrated, the tool 1000 has a proximal hand gripping end 1100 and a distal implant-gripping end 1200. The hand gripping end 1100 comprises a pair of lever arms 1110, 1120, while the implant-gripping end 1200 comprises a pair of implant-gripping jaws 1210, 1220. The arms and jaws are connected by an intermediate pivot element 1300 to provide a scissors-like actuation in which movement of the lever arms 1110, 1120 toward each other moves the gripping jaws 1210, 1220 together.

The tool 1000 may be configured to engage an anterior portion of the implant 10 (i.e. the portion associated with anterior face 18). Thus, implant-gripping jaws 1210, 1220 may comprise respective implant engaging surfaces 1212, 1222. These engaging surfaces may each further comprise an implant gripping section 1214, 1224 and an implant impaction section 1216, 1226, The implant gripping sections 1214, 1224 are configured to wrap around the anterior portion of the implant to lock the implant 10 within the jaws of the tool 1000. When gripping an implant 10, the implant impaction section 1216, 1226 is located adjacent the anterior face 18 of the implant and is configured to transmit an impaction force applied via the tool directly to the anterior face 18 of the implant 10, thus facilitating insertion of the implant between the targeted intervertebral space. As a result of this arrangement, the gripping tool conforms to the natural outer contour of the implant. Thus, the implant 10 need not incorporate additional features such as notches, grooves, or engagement holes to allow it to be gripped by the tool. Rather, a simpler overall implant design is provided, and it is also one in which the strength of the implant is not compromised by the inclusion of such notches, grooves or engagement holes.

The proximal end of the tool 1000 may be an impaction surface 1130, a portion of which is disposed at the proximal-most point of each lever arm 1110, 1120. This impaction surface 1130 may be generally flat and suitable for being impacted using a mallet or other appropriate impacting tool to aid in the insertion of the implant 10 in the targeted intervertebral space. A biasing assembly 1400 comprising a pair of leaf springs 1410, 1420 may also be provided between the lever arms 1110, 1120 to bias the arms and jaws 1210, 1220 open to make gripping and releasing the implant 10 easier.

The tool 1000 may further be provided with a grip-locking assembly 1500 comprising threaded nut 1510 and rod 1520 combination to lock the arms (and the jaws) in the gripping position. Thus, in the illustrated embodiment a first end 1522 of the rod 1520 may be pinned to an inner surface 1112 of the first lever arm 1110 and the second end 1524 may extend through a bore 1122 in the second lever arm 1120 such that at least an intermediate portion 1526 of the rod extends beyond the outer surface 1124 of the second arm 1120. Threaded nut 1510 may be adjustably located along this intermediate portion 1526 of the rod to prevent movement of the lever arms 1110, 1120 away from each other beyond a point determined by the position of the nut 1510 on the rod 1520. Typically, the surgeon may initially adjust the nut to lie adjacent the rod second end so that maximum separation of the lever arms 1110, 1120 and gripping jaws 1210, 1220 is permitted. Once the surgeon grips the implant 10, the nut 1510 may then be adjusted along the rod 1520 to a position abutting the outer surface 1124 of the second lever arm 1120, thus preventing the arms 1110, 1120 and jaws 1210, 1220 from opening and thereby locking the tool 1000 and the implant 10 together. In one embodiment, the nut 1510 is a speed-nut, which may allow quick actuation and locking of the relative position of the lever arms 1110, 1120.

In an alternative embodiment, a threaded hole (not shown) may be formed in the implant through the anterior surface 18 to receive a threaded end of an implant inserter to implant the implant between the vertebrae.

Figure 15:
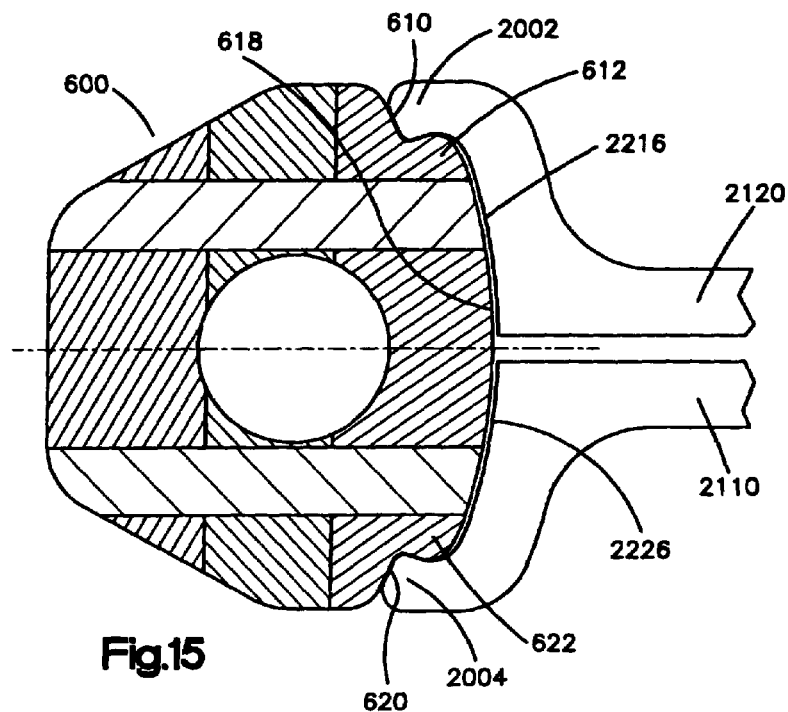
FIG. 15 is a perspective view of a seventh exemplary embodiment of the implant and an implant insertion tool according to the present invention.

A further alternative embodiment of the invention is illustrated in FIG. 15, in which implant 600 is configured so that an installation tool 2000 may engage the implant along only the implant anterior face 618, as opposed to the earlier embodiments in which the tool engages the implant by wrapping around a portion of the outer perimeter of the implant. The advantage to the present embodiment is that the implant presents a medial-laterial aspect no greater than the medial-lateral width of the implant at its widest portion. Thus, the size of the opening between the targeted vertebrae is minimized.

Implant 600 thus has tool engaging recesses 610, 620 formed at the outer edges of the anterior surface 618. These recesses 610, 620 are configured to receive correspondingly shaped tip portions 2002, 2004 of engaging tool 2000. Recesses 610 and 620 further define raised portions 612, 622 which allow the tip portions 2002, 2004 to positively axially engage the implant 600 to allow the tool 2000 to tightly engage the implant 600. Tool arms 2110, 2120 may each have an implant impaction surface 2216, 2226 configured to conform to the anterior surface 618 of the implant 600, thus allowing an impaction force applied via the tool 2000 to be evenly applied to the implant. Aside from the implant-engaging geometry, tool 2000 may be similar in all other details to tool 1000, previously described in relation to FIGS. 14A and 14B.

Figure 22A:
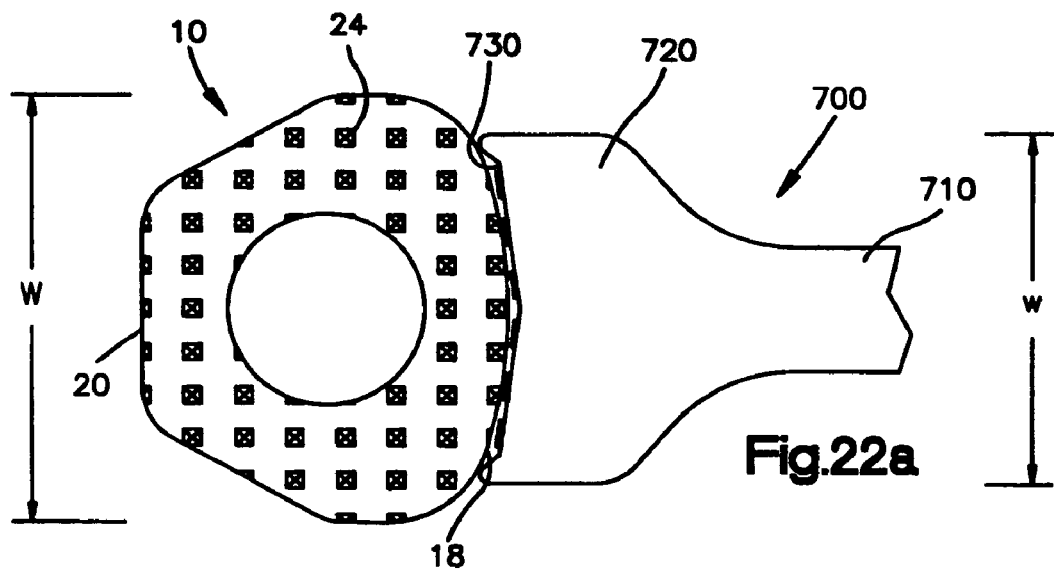
FIGS. 22a-22b are top and side views, respectively, of an impacter for use with the implant according to the present invention.
Figure 22B:
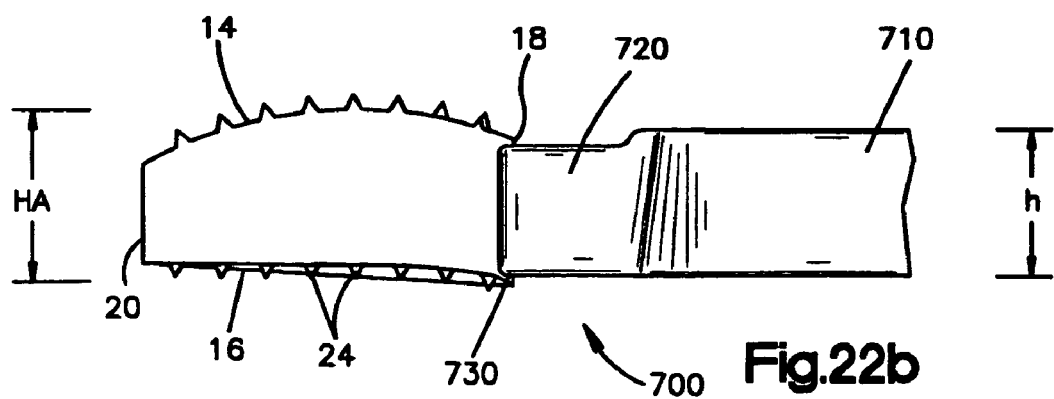

After the implant is placed between the vertebrae, an impacter may be used to precisely position and impact the implant between the vertebrae. FIGS. 22a and 22b show a top and side view, respectively, of an impacter 700 for use with any of the implants described herein. As illustrated, the impacter 700 may have a proximal hand gripping end 710 and a distal implant-engaging end 720. The impacter 700 may be configured to engage an anterior portion or segment of the implant 10 (i.e., the portion associated with the anterior face 18). The implant-engaging end 720 of the impacter 700 may have an implant-engaging face 730 at the most distal end of the impacter 700. When engaging an implant 10, the implant-engaging face 730 may be located adjacent the anterior face 18 of the implant 10 and may be configured to transmit an impaction force applied via the impacter 700 directly to the anterior face 18 of the implant 10, thus facilitating precise placement of the implant between the vertebrae. As a result of this arrangement, the impacter 700 may conform to the natural outer contour of the implant 10. Preferably, the implant-engaging end 720 is sized and dimensioned to engage the anterior face 18 of the implant 10. The implant-engaging face has a height h and a width w which may be equal to or less than the height HA and width W, respectively of the anterior surface of the implant 10.

The implant 10 need not incorporate additional features such as notches, grooves, or engagement holes to allow it to be engaged by the impacter. However, the implant-engaging face 730 of the impacter 700 may have additional features such as notches or grooves to facilitate engagement with the implant 10 during impaction. FIG. 22a shows grooves 740 in the implant-engaging-face 730. The proximal end of the impacter may be an impaction surface (not shown) similar to that of the tool 1000. In particular, the impaction surface of the impacter 700 may be generally flat and suitable for being impacted using a mallet or other appropriate impacting tool to aid in the precise positioning of the implant 10 in the intervertebral space.

In order to restore the intervertebral space to the proper size after the affected disc has been removed, implant 10 has a height sized to match the height of the removed disc. Typically for cervical discectomies, this height is between about 5 mm to about 12 mm, but other heights may be used. Implant 10 may also be configured for corpectomies. In which case, it should be noted that implants 10 may be configured so that the height of the implant would be within the range of from about 10 to about 150 mm. Other heights may also be used. These larger sizes could be used in corpectomy, a surgical procedure in which an entire vertebral body is removed, including the disc material above and below it. Alternatively, the implant 10 may be configured for a hemi-corpectomy, which involves resecting only a portion of a vertebral body. Implants 10 would be inserted in the space created by the removed section of bone.

While the embodiments described above comprise parts formed from three portions of cortical bone it will be appreciated that the invention may apply to one or more pieces of cortical bone formed together to create a unitary implant.

Further, while the invention has been described in relation to an implant formed entirely of cortical bone, it will be appreciated that any type of bone may be used, including cancellous and cortical bone, to form an implant having desired physical properties for use as a spinal fusion implant. Thus, an implant may be provided in which multiple pieces of cortical and or cancellous bone are combined in a single implant. Likewise, such an implant, or portions of such an implant, may be partially or fully demineralized, as desired to provide an implant with an increased propensity for integration with the adjacent vertebral bodies.

A method of manufacturing the inventive multipiece cortical bone implant is also provided. Implant 10 may be manufactured by first roughly shaping first, second and third portions 20, 30, 40 out of cortical allogenic bone. The portions may be oriented so that the Haversian canals of each bone portion are substantially aligned to be roughly perpendicular to the superior and inferior surfaces 14, 16 of the implant. Orienting the bone portions in this manner may provide an implant having maximum strength in the superior-inferior direction. It may also provide the benefit of readily allowing blood and/or osteogenic materials to flow through the canals between the vertebral end plates, thus speeding fusion of the implant with the adjacent vertebrae.

Male and female portions of dovetail joints 34,45 are then formed in the first, second and third portions 20,30, 40 and respectively. The bone portions are then fit together by engaging the respective male and female parts of dovetail joints 34, 45. Bores 80 and 90 for pins 60 and 70 are then formed in the first, second and third portions 30,40 and 50, and pins 60 and 70 are then inserted through the bores. If desired, adhesive may be used between portions 20,30 and 40, and/or between the portions and pins 60, 70. In one embodiment, pins 70 and 80 are sized so that there is a slight interference between the exterior surface of the pins and their respective bores 80 and 90. Pins 60, 70 are thus secured in bores 80, 90 by an interference fit. Alternatively, adhesive may be used to secure pin 50 into holes 28 and 38. In a further alternative embodiment, the respective male and female parts of the respective dovetail joints may be configured to achieve an interference fit, to facilitate locking of the pieces together. This interference fit may provide sufficient locking integrity that the implant may be used without the need for cortical pins.

Opening 22 is then formed, and the outer perimeter of the implant 10 including anterior and posterior end surfaces 18, 20 is formed using the opening as the implant centroid. To further ensure that pins 60, 70 are retained within the bone portions 20, 30, 40 the ends of each pin may be peened or staked using a suitable tool, to deform/flare the end portion of each pin.

Superior and inferior surfaces 14, 16 are then shaped into the proper desired form, be it convex, lordotic or parallel. Finally, teeth 24 are formed into the superior and inferior surfaces 14, 16. Tool-engaging surfaces such as threaded bores or recesses may also be formed at this point, if desired for a particular application.

In one embodiment, the shaping of the parts and sections of implant 10 is performed by computer-controlled milling. However, alternative methods of forming the various parts of implant 10 may also be used.

To facilitate osteointegration of the implant with the adjacent vertebral bodies, the implant may be partially demineralized either before or after assembly. Such demineralization may improve the osteoinductive properties of the cortical bone, thus speeding the fusion process. Since demineralized cortical bone is generally weaker than fully mineralized cortical bone, the implant my be only partially demineralized. Thus, providing a partially demineralized cortical implant may result in an implant having the desired increased osteoconductive properties without a significant decrease in implant strength. Such demineralization may be provided using any known method, including controlled immersion in a hydrochloric acid (HCI) solution, or a loop flushing technique in which HCI solution is circulated over or through at least a portion of the implant.

Furthermore, while a partially demineralized implant is disclosed, it will be appreciated that any appropriate demineralization scheme may be provided to obtain a cortical implant having the desired structural and osteointegrative properties.

Once the implant has been fully formed, and, where appropriate, partially demineralized, the implant may be freeze dried and packaged for storage and shipping. Prior to implantation in a patient, the implant should be rehydrated by immersing the implant in a saline solution for a period of up to about 60 minutes. Rehydration may be performed using saline solution, blood, bone marrow, or any other appropriate fluid. Antibiotics or other pharmacologically active materials may also be applied to the implant at this time, and such materials may be added before, during or after the rehydration step.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

The invention claimed is:

1. A multipiece implant comprising:

a body having a superior surface, an inferior surface and a surface extending from the superior surface to the inferior surface, the body further including a central opening extending from the superior surface to the inferior surface for receiving one of osteogenic, osteoconductive or osteoinductive material;

the body being formed from at least first and second mating cortical bone segments, each segment having a locking surface configured to engage the locking surface of the other segment, each segment including at least a portion of the superior and inferior surfaces of the body and at least two passages, the first and the second cortical bone segments being arranged so that, when mated, the passages are in registry and have a common axis;

at least two cortical bone pins disposed within the passages;

wherein the locking surfaces of the first and second bone segments form dovetail joints, each of the dovetail joints including a mortise and a tenon, each of the passages passing through one of the mortises and tenons so that the cortical bone pins pass through one of the mortises and tenons;

and wherein the passages are configured so that the bone pins are positioned on opposite sides of the central opening.

2. The multipiece implant of claim 1, wherein the superior and inferior surfaces of each cortical bone segment comprise a plurality of teeth.

3. The multipiece implant of claim 2, wherein the teeth are arranged in a two dimensional array, and at least some of the teeth have a pyramidal shape.

4. The multipiece implant of claim 1, wherein the superior surface has a substantially convex curvature.

5. The multipiece implant of claim 4, wherein the inferior surface has a substantially convex curvature.

6. The multipiece implant of claim 5, wherein the curvature of the superior surface lies in an anterior-posterior plane, and the curvature of the inferior surface lies in a medial-lateral plane.

7. The multipiece implant of claim 4, wherein the superior and inferior surfaces each comprise a series of teeth.

8. The multipiece implant of claim 7, wherein the teeth are arranged in a two dimensional array, and the teeth have a pyramidal shape.

9. The multipiece implant of claim 1, the implant further comprising an anterior-posterior axis, the at least two passages being aligned substantially parallel to the anterior-posterior axis.

10. The multipiece implant of claim 1, the implant further comprising an anterior-posterior axis, wherein the at least two passages are non-parallel to the anterior-posterior axis.

11. The multipiece implant of claim 10, wherein an angle between the at least two passages and the anterior-posterior axis is between about 9 degrees to about 18 degrees.

12. The multipiece implant of claim 1, wherein the at least two passages each include an abutting surface configured to engage an end surface of the cortical pins.

13. The multipiece implant of claim 12, the first and second bone segments comprising an anterior bone segment and a center bone segment, respectively the implant further comprising a posterior bone segment engaged to the center bone segment via a dovetail joint, wherein the abutting surface is located in the posterior bone segment so that when the implant is placed between vertebral end plates of a patient, the pins are thereafter prevented from migrating in the posterior direction.

14. The multipiece implant of claim 12, the first and second bone segments comprising an anterior bone segment and a center bone segment, the implant further comprising a posterior bone segment engaged to the center bone segment via a dovetail joint, wherein the abutting surface is located in the anterior bone segment so that when the implant is placed between vertebral end plates of a patient, the pins are thereafter prevented from migrating in the anterior direction.

15. The multipiece implant of claim 1, wherein the at least one mortise has a first engaging face and the at least one tenon has a second engaging face which, when the mortise and tenon are oriented as when engaged, is not parallel to the first engaging face.

16. The multipiece implant of claim 15, wherein, when the mortise and the tenon oriented as when engaged, the first and second engaging faces define an angle of about 2 degrees.

17. The multipiece implant of claim 1, wherein the at least two cortical bone pins do not intersect either of the superior and inferior surfaces.

18. A multipiece intervertebral implant for implantation between first and second vertebrae, the implant comprising:
a first segment constructed of cortical bone and having a first coupling portion;
a second segment constructed of cortical bone and having second and third coupling portions; and
a third segment constructed of cortical bone and having a fourth coupling portion;
wherein the first and second segments are joined together by interfitting the first and second coupling portions and wherein the second and third segments are joined together by interfitting the third and fourth coupling portions to form a single body, the single body including a superior surface, an inferior surface and a surface extending from the superior surface to the inferior surface, the single body further including a central opening extending from the superior surface to the inferior surface;
wherein the first and second coupling portions and the third and fourth coupling portions are dovetail joints, each of the dovetail joints including a corresponding mortise and tenon; and
wherein each bone segment forms at least a portion of the superior surface and at least a portion of the inferior surface; and
wherein the single body includes a first bore extending at least partially through each of the first, second, and third bone segments and a second bore extending at least partially through each of the first, second, and third bone segments, the first and second bores being configured to receive first and second bone pins, respectively, the first and second bone pins being arranged so that the first and second bone pins do not intersect the central opening; the first bone pin positioned on one side of the central opening and the second bone pin positioned on an opposite side of the central opening, each of the first and second bone pins passing through one of the mortises and tenons.

19. The multipiece implant of claim 18, wherein the superior surface is convexly curved.

20. The multipiece implant of claim 18, wherein the inferior surface is substantially flat.

21. The multipiece implant of claim 18, wherein the central opening has a substantially larger diameter than each of the first and second bores.

22. The multipiece implant of claim 18, wherein at least one of the first, second, and third bone segments is at least partially demineralized.

23. The multipiece implant of claim 18, wherein at least a portion of the implant comprises teeth having a pyramidal shape.

24. The multipiece implant of claim 18, wherein the first and second bores extend completely through each of the first, second, and third bone segments.

25. The multipiece implant of claim 18, wherein the first and second bores extend only partially through at least one of the bone segments.

26. The multipiece implant of claim 18, the implant further comprising an anterior posterior axis, wherein an angle between the axis of the first and second bores and the anterior-posterior axis is between about 12 degrees to about 18 degrees.

27. The multipiece implant of claim 18, wherein the central opening is partially formed in the first segment and partially formed in the second segment.

28. The multipiece implant of claim 18, wherein the first and second bone pins do not intersect either of the superior and inferior surfaces.

* * * * *